US012643286B2

(12) United States Patent
Sakata et al.

(10) Patent No.: US 12,643,286 B2
(45) Date of Patent: Jun. 2, 2026

(54) METHOD FOR PRODUCING THREE-DIMENSIONAL MANUFACTURED PRODUCT

(71) Applicant: TOKUYAMA DENTAL CORPORATION, Tokyo (JP)

(72) Inventors: Eibu Sakata, Tokyo (JP); Kei Nakashima, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 132 days.

(21) Appl. No.: 18/290,637

(22) PCT Filed: Jul. 15, 2022

(86) PCT No.: PCT/JP2022/027871
§ 371 (c)(1),
(2) Date: Jan. 19, 2024

(87) PCT Pub. No.: WO2023/008233
PCT Pub. Date: Feb. 2, 2023

(65) Prior Publication Data
US 2025/0083380 A1 Mar. 13, 2025

(30) Foreign Application Priority Data
Jul. 30, 2021 (JP) ................................. 2021-125244

(51) Int. Cl.
| | |
|---|---|
| *B29C 64/124* | (2017.01) |
| *A61K 6/884* | (2020.01) |
| *B29C 64/386* | (2017.01) |
| *B33Y 10/00* | (2015.01) |
| *B33Y 40/20* | (2020.01) |
| *B33Y 50/00* | (2015.01) |
| *B33Y 70/10* | (2020.01) |
| *C08F 2/48* | (2006.01) |

(52) U.S. Cl.
CPC ............ *B29C 64/124* (2017.08); *A61K 6/884* (2020.01); *B29C 64/386* (2017.08); *C08F 2/48* (2013.01); *B33Y 10/00* (2014.12); *B33Y 40/20* (2020.01); *B33Y 50/00* (2014.12); *B33Y 70/10* (2020.01)

(58) Field of Classification Search
CPC ..... B29C 64/124; B29C 64/386; A61K 6/884; A61K 6/887; C08F 2/48; C08F 2/50; B33Y 10/00; B33Y 40/20; B33Y 50/00; B33Y 70/10; B33Y 80/00; A61C 13/0013; A61C 13/0006
See application file for complete search history.

(56) References Cited

U.S. PATENT DOCUMENTS

| | | | | |
|---|---|---|---|---|
| 2020/0362157 A1* | 11/2020 | Parkar | .................... | B33Y 80/00 |
| 2020/0390527 A1* | 12/2020 | Niwa | ................. | A61C 13/0013 |
| 2022/0251275 A1* | 8/2022 | Suzuki | ............. | C08F 220/1811 |

FOREIGN PATENT DOCUMENTS

| | | |
|---|---|---|
| JP | 2016-525150 A | 8/2016 |
| JP | 2018-076455 A | 5/2018 |
| JP | 2020-158417 A | 10/2020 |
| JP | 2021-504511 A | 2/2021 |
| RU | 2275183 C2 | 4/2006 |
| RU | 2557961 C2 | 7/2015 |
| RU | 2686748 C1 | 4/2019 |
| WO | 2019/048963 A1 | 3/2019 |
| WO | 2019103855 A1 | 5/2019 |
| WO | 2020/235628 | 11/2020 |

OTHER PUBLICATIONS

Extended European Search Report issued in counterpart European Patent Application No. 22849296.3 mailed Oct. 24, 2024 (6 pages).
Office Action issued in related Russian Patent Application No. 2024101293, issued Sep. 15, 2025, with translation (12 pages).
International Search Report issued in corresponding International Application No. PCT/JP2022/027871 mailed Aug. 23, 2022 (5 pages).
Written Opinion issued in corresponding International Application No. PCT/JP2022/027871 mailed Aug. 23, 2022 (4 pages).

* cited by examiner

*Primary Examiner* — Michael M. Robinson
(74) *Attorney, Agent, or Firm* — Osha Bergman Watanabe & Burton LLP

(57) ABSTRACT

Provided is a method for producing a three-dimensional manufactured product, the method including: a shaping step of performing a vat photopolymerization process using a liquid photocurable composition containing a radically-polymerizable monomer, an inorganic filler, a photopolymerization initiator, an activating light absorbent, and a polymerization inhibitor, to obtain a shaped product having a shape corresponding to the shape of a target article and containing an effective amount of the photopolymerization initiator in the interior thereof; and a post-polymerization step of irradiating the shaped product with activating light at an irradiation intensity of 10 to 10,000 mW/cm², and then heating the shaped product at a temperature of 50° C. or higher and lower than 110° C., to polymerize an unpolymerized component contained in the shaped product. Further, provided is a method for producing a dental restoration, including producing the dental restoration according to this method for producing a three-dimensional manufactured product.

4 Claims, No Drawings

METHOD FOR PRODUCING THREE-DIMENSIONAL MANUFACTURED PRODUCT

TECHNICAL FIELD

The present invention relates to a method for producing a three-dimensional manufactured product.

BACKGROUND ART

A technique of producing a three-dimensional manufactured product by curing a photocurable resin by irradiation with light is known as photofabrication. Among the photofabrication processes, there are widely known a vat photopolymerization process where a photocurable resin placed in a vat-shaped container is irradiated with light to achieve the manufacturing, and a material jetting process where a photocurable resin is ejected by an ink-jet printer and the ejected photocurable resin is concurrently irradiated with light to achieve the manufacturing. In the production of three-dimensional manufactured products by such photofabrication processes, in order to shorten the manufacturing time, photofabrication by brief irradiation with light is commonly performed to obtain a shaped product having an insufficient extent of polymerization and low strength between the manufactured layers (also referred to as "manufacturing stage" or "shaping step"), followed by washing the shaped product, and then final curing by additional irradiation with light and/or heating.

In the dental field, dental restorations such as dentures and crown prostheses need to be produced highly precisely such that the dental restorations have a unique shape in accordance with the situation in the oral cavity of each individual patient, and photofabrication based on computer aided design (CAD) data designed on the basis of digital data obtained by oral scanning or the like can easily produce a three-dimensional manufactured product that reproduces the designed shape with high precision. Dental restorations to be used in the oral cavity require such a high precision that they fit upon their application in the oral cavity of each individual patient, and thus, sufficient curing in the final curing is necessary. However, there is a problem that cracks are likely to be generated in the interior and/or on the surface of the three-dimensional manufactured product due to deformation caused by polymerization shrinkage during the final curing and stresses caused by the deformation between the layers manufactured during the photofabrication.

Therefore, solutions for suppressing the occurrence of such a problem have been studied. For example, Patent Document 1 describes "a preparing method of a dental three-dimensional modeled object, wherein the method does not comprise a step of a final curing, by a light and/or heating type post-curing device, a dental three-dimensional modeled object modeled by any stereolithography-type three-dimensional printing machine under recommended conditions, using 'a dental stereolithography-type three-dimensional printing material comprising at least one or more (a) monofunctional acrylate monomer having an aromatic ring and (b) photopolymerization initiator, wherein an electronegativity difference between adjacent atoms which are bonded by covalent bond in all atoms constituting the (a) monofunctional acrylate monomer having an aromatic ring is less than 1.00'".

Patent Document 2 describes as a composition suitable for producing denture bases and a set of artificial teeth by three-dimensional (3D) printing, "a composition comprising: a light-curable viscous mixture comprising: 0 to 50% by weight of a solution having a polymerized poly(methyl methacrylate) dissolved in methyl methacrylate monomer solvent; 5 to 20% by weight of at least one kind of polyfunctional aliphatic (meth)acrylate; 5 to 40% by weight of at least one kind of aliphatic urethane (meth)acrylate oligomer; 25 to 65% by weight of at least one kind of difunctional bisphenol-A dimethacrylate; 0.1 to 5% by weight of at least one kind of a photoinitiator; 0.05 to 2% by weight of at least one kind of light stabilizer; and 0.1 to 3% by weight of color pigment based on the total weight of the composition".

Furthermore, in relation to a technique for suppressing polymerization shrinkage during the final curing, without limitation to the dental field, Patent Document 3 describes "a composition for optical stereolithography comprising: (A) a cationically-polymerizable aromatic compound having two or more aromatic rings and three or more glycidyl ether structures; (B) a cationically-polymerizable aliphatic compound having one or more alcoholic hydroxyl groups and two or more glycidyl ether structures and/or a cationically-polymerizable compound having an oxetane group; (C) a radically-polymerizable compound having one or more alcoholic hydroxyl groups and two or more methacrylic and/or acrylic groups; (D) a cationic polymerization initiator which is a sulfonium compound or a bis(alkylphenyl) iodonium compound; (E) a radical polymerization initiator; and (F) a sensitizer, wherein the composition comprises 10 to 50 mass % of the (A) cationically-polymerizable aromatic compound, 1 to 30 mass % of the (B) cationically-polymerizable aliphatic compound and/or cationically-polymerizable compound having an oxetane group, 10 to 40 mass % of the (C) radically-polymerizable compound, 0.1 to 20% by mass of the (D) cationic polymerization initiator, 0.1 to 20% by mass of the (E) radical polymerization initiator, and 0.05 to 5% by mass of the (F) sensitizer".

CITATION LIST

Patent Document

Patent Document 1: Japanese Unexamined Patent Application, Publication No. 2020-158417

Patent Document 2: Japanese Unexamined Patent Application, Publication No. 2016-525150

Patent Document 3: Japanese Unexamined Patent Application, Publication No. 2018-76455

DISCLOSURE OF THE INVENTION

Problems to be Solved by the Invention

According to the technique described in Patent Document 1, in the production of a dental three-dimensional modeled object such as a dental prosthesis by a 3D printer, a dental three-dimensional modeled object having excellent dimensional accuracy can be reportedly obtained by achieving a high degree of polymerization in a manufacturing stage (shaping step). However, the stereolithographic method actually employed in Patent Document 1 is a material jetting method employing an ink jet printing, and the dental stereolithography-type three-dimensional printing material used therein contains no or an extremely small amount of, if any, inorganic filler. Therefore, when this technique is used to produce a dental prosthesis, such a high mechanical strength that the dental prosthesis undergoes no break, fracture, or the like in the presence of the occlusal pressure, etc. in use is difficult to realize.

In the composition described in Patent Document 2, the reduction of an amount of shrinkage during the photofabrication and the suppression of cracks in the interior and on the surface of the three-dimensional manufactured product are achieved by adding polymerized poly(methyl methacrylate), specifically, polymethylmethacrylate having a molecular weight of 10,000 or more. However, the addition of such a polymer component to the composition tends to decrease the strength of the three-dimensional manufactured product. Further, such addition also tends to increase the viscosity of the composition; thus, when an inorganic filler is added for achieving high strength, the viscosity of the composition greatly increases, leading to the difficulty in handling.

Furthermore, in the composition for optical stereolithography described in Patent Document 3, the reduction of the polymerization shrinkage is intended by using the radically-polymerizable monomer and the cationically-polymerizable monomers in combination, but the cationic polymerization system is susceptible to moisture, and the manufacturing may be difficult depending on the storage environment of the composition and the environment during the manufacturing. In addition, when an inorganic filler is added for achieving high strength, the interaction with the inorganic filler makes the manufacturing difficult.

Accordingly, it is an object of the present invention to provide a method for producing a three-dimensional manufactured product including a cured product of a photocurable resin composition containing a large amount of an inorganic filler for achieving high strength, in which the method achieves the suppression of deformation due to polymerization shrinkage, generation of cracks in the interior of the manufactured product caused by the deformation, etc., and in turn, allows for the production of a three-dimensional manufactured product with high accuracy and high strength.

Means for Solving the Problems

Specific means for solving the above problems include the following embodiments.

A first aspect of the present invention relates to a method for producing a three-dimensional manufactured product, the method comprising:

a shaping step of digitizing and ordinating a three-dimensional object in a height direction of the three-dimensional object and generating two-dimensional shape data indicating the cross-sectional shape of the three-dimensional object at each ordinated height, based on three-dimensional shape data indicating the shape of the three-dimensional object, and sequentially forming and stacking manufactured layers each having a shape corresponding to the two-dimensional shape at each height based on the two-dimensional shape data, according to the order of the ordinating, using a vat photopolymerization process wherein a predetermined position of a liquid photocurable resin composition held in a vat is irradiated with activating light being ultraviolet light or visible light to selectively cure the liquid photocurable resin composition present in the position, to obtain a shaped product comprising a cured product of the liquid photocurable resin composition having a shape corresponding to the shape of the three-dimensional object; and a post-polymerization step of polymerizing an unpolymerized component comprised in the shaped product, wherein the liquid photocurable resin composition comprises: 100 parts by mass of a radically-polymerizable monomer (a); 5.0 to 400 parts by mass of an inorganic filler (b); 0.05 to 10.0 parts by mass of a photopolymerization initiator (c) that absorbs the activating light to generate a radical; 0.01 to 2.7 parts by mass of an activating light absorbent (d) that absorbs the activating light; and 0.01 to 5.0 parts by mass of a polymerization inhibitor (e), and wherein in the shaping step, the shaped product comprising an effective amount of the photopolymerization initiator is obtained, and the post-polymerization step comprises irradiating the shaped product with the activating light at an irradiation intensity of 10 to 10,000 mW/cm$^2$ and then heating the shaped product irradiated with the activating light at a temperature of 50° C. or higher and lower than 110° C.

A second aspect of the present invention relates to the method for producing a three-dimensional manufactured product according to the first aspect of the present invention, wherein the vat photopolymerization process comprises:

a first step of irradiating a predetermined position of the liquid photocurable resin composition held in the vat with the activating light and curing the liquid photocurable resin composition, based on the two-dimensional shape data at a first ordinate height in an ordinating order, to form a manufactured layer having a shape corresponding to the two-dimensional shape data, wherein the manufactured layer is a prebonding layer;

a second step of moving the prebonding layer upward or downward to supply the liquid photocurable resin composition directly above or below the prebonding layer in the vat;

a third step of irradiating a predetermined position of the liquid photocurable resin composition supplied directly above or below the prebonding layer with the activating light and curing the liquid photocurable resin composition, based on two-dimensional shape data at a height of the next ordinate in the ordinating order following the immediately preceding step, and thereby forming a new manufactured layer having a shape corresponding to the two-dimensional shape data, and concurrently bonding the new manufactured layer to the prebonding layer, to obtain a stack having the new manufactured layer as a new prebonding layer; and a fourth step of moving the stack upward or downward to supply the liquid photocurable resin composition directly above or below the new prebonding layer in the vat, and a cycle consisting of the third step and the fourth step is repeated using the new prebonding layer as the prebonding layer in the third step, and in the last third step, a new manufactured layer is formed based on two-dimensional shape data at a height of the last ordinate in the ordinating order, to obtain a stack.

A third aspect of the present invention relates to the method for producing a three-dimensional manufactured product according to the first or second aspect of the present invention, further comprising a washing step of washing the shaped product after the shaping step and before the post-polymerization step.

A fourth aspect of the present invention relates to the method for producing a three-dimensional manufactured product according to any one of the first to third aspects of the present invention, wherein the liquid photocurable resin composition comprising the activating light absorbent (d) in an amount of 20 to 90% by mass relative to the amount of the photopolymerization initiator (c), and the polymerization inhibitor (e) in an amount of 5 to 150% by mass relative to the amount of the photopolymerization initiator (c) is used to obtain the shaped product comprising an effective amount of the photopolymerization initiator (c) in the shaping step.

A fifth aspect of the present invention relates to a method for producing a dental restoration, comprising producing the dental restoration according to the method for producing a three-dimensional manufactured product according to any one of the first to fourth aspects of the present invention.

Effects of the Invention

The production method according to the present invention makes it possible to produce a three-dimensional manufactured product having excellent mechanical strength and favorable shape accuracy, and being substantially crack free in the interior thereof.

PREFERRED MODE FOR CARRYING OUT THE INVENTION

The present inventors considered that a three-dimensional manufactured product having a desired shape could be obtained using a photocurable resin composition containing a large amount of an inorganic filler by employing a vat photopolymerization process as a photofabrication method and designing CAD data in consideration of the amount of polymerization shrinkage in the post-polymerization step, and studied this strategy. However, when radically-polymerizable monomers such as (meth)acrylate monomers, which are widely used as raw materials for dental restorations, are used as polymerizable monomers, generation of cracks due to rapid polymerization shrinkage in the post-polymerization step was inevitable. In view of this, a method for suppressing the rapid polymerization shrinkage in the post-polymerization step was intensively studied. As a result of the studies, the inventors found that, when specific amounts of an activating light absorbent and a polymerization inhibitor were added to a photocurable resin composition containing a radically-polymerizable monomer, an inorganic filler, and a photopolymerization initiator (which functions upon irradiation with activating light), and the photopolymerization initiator was not completely consumed in the shaping step and an effective amount of the photopolymerization initiator was left, the crack generation could be prevented by employing specific conditions in the post-polymerization step, thus completing the present invention.

More specifically, in the method for producing a three-dimensional manufactured product according to the present embodiment, the satisfaction of the following requirements 1 to 3 is crucial.

[Requirement 1] The liquid photocurable resin composition contains: 100 parts by mass of a radically-polymerizable monomer (a); 5.0 to 400 parts by mass of an inorganic filler (b); 0.05 to 10.0 parts by mass of a photopolymerization initiator (c) that absorbs activating light to generate a radical; 0.01 to 2.7 parts by mass of an activating light absorbent (d) that absorbs the activating light; and 0.01 to 5.0 parts by mass of a polymerization inhibitor (e).

[Requirement 2] A shaped product containing an effective amount of photopolymerization initiator is obtained in the shaping step.

[Requirement 3] The post-polymerization step includes irradiating the shaped product with activating light at an irradiation intensity of 10 to 10,000 mW/cm$^2$ and then heating the shaped product irradiated with the activating light at a temperature of 50° C. or higher and lower than 110° C.

The reasons for the suppression of the crack generation in the post-polymerization step by virtue of the satisfaction of such requirements are not clear, but the present inventors presume as follows. It is believed that a portion with a low conversion (low conversion portion) exists in a bonded portion of successive layers manufactured in the shaping step, or in a boundary portion of an irradiated region upon the application of the irradiation light along with sequential change of the irradiated position, and the low conversion portion is destroyed due to shrinkage in the post-polymerization step, causing the cracks. Therefore, an increase in polymerization activity in the shaping step would increase the strength of the low conversion portion, in turn, leading to the suppression of the generation of the cracks. On the other hand, excessively high polymerization activity in the shaping step would result in the absence of an effective amount of the photopolymerization initiator in the shaped product, and hence an insufficient increase in the conversion in the post-polymerization step, leading to insufficient mechanical strength of the resultant three-dimensional manufactured product. In view of this, the producing method that satisfies the above requirements 1 to 3 is presumed to enable a three-dimensional manufactured product being substantially crack free and having high mechanical strength to be obtained.

As described above, the method for producing a three-dimensional manufactured product according to the present embodiment is characterized in that the requirements 1 to 3 described above are satisfied in the vat photopolymerization process. Thus, in the following, the vat photopolymerization process and the requirements 1 to 3 will be described in detail. It should be noted that in this specification, the expression "x to y" using numerical values x and y is intended to mean "x or more and y or less" unless otherwise specified. In this notation, when only the numerical value y is accompanied by a unit, the unit shall also apply to the numerical value x. Further, in this specification, the term "(meth)acrylate" means both "acrylate" and "methacrylate". Similarly, the term "(meth)acryloyl" means both "acryloyl" and "methacryloyl".

<Vat Photopolymerization Process, as Well as Shaping Step and Post-Polymerization Step>

As described above, the method for producing a three-dimensional manufactured product according to the present embodiment employs the so-called "vat photopolymerization process". In this regard, the vat photopolymerization process means a method in which a height direction of a three-dimensional object is digitized and ordinated and two-dimensional shape data indicating the cross-sectional shape of the three-dimensional object at each ordinated height is generated based on three-dimensional shape data indicating the shape of the three-dimensional object, and a predetermined position of a liquid photocurable resin composition held in a vat is irradiated with activating light being ultraviolet light or visible light to selectively cure the liquid photocurable resin composition present in that position.

In the vat photopolymerization process, three-dimensional shape data defining the shape of a shaped product can be easily obtained in the form of digital data by scanning the outer front surface of an article having a target three-dimensional shape or the inner surface of a mold for the article using a 3D scanner or a three-dimensional digitizer. Three-dimensional shape digital data produced by CAD or the like can also be used. For example, when producing a dental prosthesis for tooth restoration in a specific patient, three-dimensional shape (digital) data obtained by 3D-scanning using an intraoral scanner can be suitably used.

The three-dimensional shape (digital) data obtained thus is divided (digitalized) discontinuously at predetermined minute intervals (height width), usually a height width of tens to hundreds of micrometers, in the height direction of the three-dimensional object by means of, for example, CAD, and ordinated in the height direction to generate two-dimensional shape data indicating the cross-sectional shape of the three-dimensional object at each ordinated height.

Then, a photofabrication apparatus having a vat for storing the liquid photocurable resin composition and a light source for emitting the activating light is used to irradiate, with the activating light, a position of the liquid photocurable resin composition determined based on the two-dimensional shape data and selectively cure the portion irradiated with the light, to obtain a shaped product made of a cured product of the liquid photocurable resin composition (shaping step). In other words, the manufactured layers each having a shape corresponding to the two-dimensional shape at each height are sequentially formed and stacked according to the order of the ordinating based on the two-dimensional shape data, to obtain a shaped product made of a cured product of the liquid photocurable resin composition having the shape corresponding to the shape of the three-dimensional object.

The shaping step will be described in more detail. First, the predetermined position of the liquid photocurable resin composition held in the vat is irradiated with the activating light and cured based on the two-dimensional shape data at a first ordinate height in an ordinating order, to form a manufactured layer having a shape corresponding to the two-dimensional shape data, and the manufactured layer is used as a prebonding layer (or, layer to be bonded) (first step). Next, the prebonding layer is moved upward or downward to supply the liquid photocurable resin composition directly above or below the prebonding layer in the vat (second step). Next, a predetermined position of the liquid photocurable resin composition supplied directly above or below the prebonding layer is irradiated with the activating light and cured based on the two-dimensional shape data at a height of the next ordinate in the ordinating order following the immediately preceding step, to form a new manufactured layer having a shape corresponding to the two-dimensional shape data, and the new manufactured layer is bonded to the prebonding layer, to obtain a stack having the new manufactured layer as a new prebonding layer (third step). Then, the stack is moved upward or downward to supply the liquid photocurable resin composition directly above or below the new prebonding layer in the vat (fourth step), and a cycle consisting of the third step and the fourth step is repeated using the new prebonding layer as the prebonding layer in the third step, and in the last third step, a new manufactured layer is formed based on the two-dimensional shape data at a height of the last ordinate in the ordinating order, to obtain a stack, and the finally obtained stack is the shaped product mentioned above.

As the vat photopolymerization process, a StereoLithography (SLA) method, a Digital Light Processing (DLP) method, a Liquid Column Display (LCD) method, and the like are known depending on a difference in method of light irradiation. In the method for producing a three-dimensional manufactured product according to the present embodiment, these methods can be employed without limitation. Additionally, the photofabrication apparatus is not limited as long as it is for the vat photopolymerization process, and any apparatus suitable for a method employed can be used. Incidentally, monochromatic light having a specific single wavelength peak or light having a relatively narrow wavelength distribution may be used as the activating light for the irradiation, or a plurality of types of light having different peak wavelengths may also be used. In particular, a photofabrication apparatus for the SLA method is preferably used from the viewpoint of obtaining a three-dimensional manufactured product with higher definition and higher strength.

The shaped product thus obtained is washed as necessary, and then the unpolymerized component(s) contained in the shaped product is (are) polymerized via additional light irradiation and/or heating, etc. (post-polymerization step).

<Requirement 1>

In the method for producing a three-dimensional manufactured product according to the present embodiment, it is necessary to use, as the liquid photocurable resin composition in the shaping step, a liquid photocurable resin composition containing:

100 parts by mass of a radically-polymerizable monomer (a); 5.0 to 400 parts by mass of an inorganic filler (b); 0.05 to 10.0 parts by mass of a photopolymerization initiator (c) that absorbs activating light to generate a radical; 0.01 to 2.7 parts by mass of an activating light absorbent (d) that absorbs the activating light; and 0.01 to 5.0 parts by mass of a polymerization inhibitor (e).

Incidentally, the liquid photocurable resin composition preferably has a low viscosity in order to manufacture a shaped product with high accuracy and prevent the presence of air bubbles, etc. in the shaped product. On the other hand, generally, an overly low viscosity of the resin composition before curing tends to yield a cured product having low strength. For this reason, the liquid photocurable resin composition has a viscosity at 25° C. of preferably 5 to 50,000 mPa·s, and particularly 10 to 30,000 mPa·s.

The components of the liquid photocurable resin composition and the blending amount thereof will be described below.

[(a) Radically-Polymerizable Monomer]

Any monomer having radically-polymerizable nature can be used as the radically-polymerizable monomer (a) without limitation, and a (meth)acrylate monomer is preferably used because of its high curing speed and the excellent strength of the three-dimensional manufactured product obtained therefrom.

Any of a monofunctional (meth)acrylate, a bifunctional (meth)acrylate, and a trifunctional or higher polyfunctional (meth)acrylate may be used as the (meth)acrylate monomer, and in order to produce a three-dimensional manufactured product having higher strength, a bifunctional or higher polyfunctional (meth)acrylate preferably accounts for 50% by mass or more, particularly 80% by mass or more, based on the total mass of all the radically-polymerizable monomers. The proportion of the bifunctional or higher polyfunctional (meth)acrylate is more preferably 95% by mass.

Examples of preferably used bifunctional or higher polyfunctional (meth)acrylates include: bisphenol A skeleton-containing (meth)acrylates such as 2,2'-bis {4-[3-(meth)acryloyloxy-2-hydroxypropoxy]phenyl}propane, 2,2'-bis [4-(meth)acryloyloxyphenyl]propane, and 2,2'-bis [4-(meth)acryloyloxypolyethoxyphenyl]propane; ethylene glycol-based (meth)acrylates such as triethylene glycol dimethacrylate and ethylene glycol dimethacrylate; aliphatic di(meth)acrylates such as 1,3-propanediol di(meth)acrylate and 1,9-nonanediol dimethacrylate; urethane group-containing (meth)acrylates such as 1,6-bis(methacryloyloxy-2-ethoxycarbonylamino)-2,2,4-trimethylhexane; trifunctional (meth)acrylates such as trimethylolpropane trimethacrylate; isocyanate skeleton-containing (meth)acrylates such as tris (2-methacryloyloxyethyl) isocyanurate; and the like. Among these, 2,2'-bis [4-(meth)acryloyloxyphenyl]propane, 2,2'-bis [4-(meth)acryloyloxypolyethoxyphenyl]propane, triethylene glycol dimethacrylate, tris(2-methacryloyloxyethyl) isocyanurate or the like is preferably used because of their low viscosity and the excellent strength of the three-dimensional manufactured product obtained therefrom.

Examples of the monofunctional (meth)acrylate suitable for use in combination with the bifunctional or higher polyfunctional (meth)acrylate include methyl (meth)acrylate, ethyl (meth)acrylate, isopropyl (meth)acrylate, hydroxyethyl (meth)acrylate, tetrahydrofurfuryl (meth)acrylate, glycidyl (meth)acrylate, and the like.

Incidentally, these radically-polymerizable monomers may be used singly or in combination of two or more types thereof.

[(b) Inorganic Filler]

The liquid photocurable resin composition needs to contain 5 to 400 parts by mass of the inorganic filler (b) relative to 100 parts by mass of the radically-polymerizable monomer (a) in order to increase the mechanical strength such as the rigidity of the resultant three-dimensional manufactured product. An overly high content of the inorganic filler (b) leads to an overly high viscosity of the liquid photocurable resin composition. On the other hand, an overly low content of the inorganic filler (b) results in insufficient mechanical strength of the resultant three-dimensional manufactured product. Therefore, the content of the inorganic filler (b) is preferably 10 to 300 parts by mass, and more preferably 20 to 200 parts by mass, relative to 100 parts by mass of the radically-polymerizable monomer (a).

The material of the inorganic filler (b) is not limited, and for example, any material for use as a filler for tooth restoration materials may be used. Specifically, examples of the material of the inorganic filler (b) which is employed include: elementary substances of metal; metal oxides or metal composite oxides; metal salts such as fluorides, carbonates, sulfates, silicates, hydroxides, chlorides, sulfites, phosphates of metals; complexes of these metal salts; and the like. Preferably, the following materials are employed: metal oxides such as amorphous silica, quartz, alumina, titania, zirconia, barium oxide, yttrium oxide, lanthanum oxide, and ytterbium oxide; silica-based composite oxides such as silica-zirconia, silica-titania, silica-titania-barium oxide, and silica-titania-zirconia; glass materials such as borosilicate glass, aluminosilicate glass, and fluoroaluminosilicate glass; metal fluorides such as barium fluoride, strontium fluoride, yttrium fluoride, lanthanum fluoride, and ytterbium fluoride; inorganic carbonates such as calcium carbonate, magnesium carbonate, strontium carbonate, and barium carbonate; metal sulfates such as magnesium sulfate and barium sulfate; and the like. In the production of a dental restoration, particles of silica-zirconia, silica-titania, silica-titania-barium oxide, silica-titania-zirconia or the like are preferably used because of their strong X-ray contrast properties. Silica-zirconia particles are most preferably used from the viewpoint of the wear resistance of the cured product.

The average particle diameter of the inorganic filler (b) is not limited, and fillers having an average particle diameter of 0.01 to 100 μm (preferably 0.01 to 10 μm), which are commonly used as a tooth restoration material, may be appropriately used depending on the purposes. Several of these fillers may be used in combination, and several fillers with different average particle diameters may be used in combination. Furthermore, the inorganic filler (b) may be added in the form of the so-called organic-inorganic composite filler.

Incidentally, the inorganic filler (b) is desirably treated with a surface treating agent typified by a silane coupling agent in order to improve the compatibility of the inorganic filler (b) with the polymerizable monomer and improve the mechanical strength and water resistance of the product. The surface treatment may be performed according to any known method. Examples of the silane coupling agent preferably used include methyltrimethoxysilane, methyltriethoxysilane, methyltrichlorosilane, dimethyldichlorosilane, trimethylchlorosilane, vinyltrichlorosilane, vinyltriethoxysilane, vinyltris(β-methoxyethoxy) silane, γ-methacryloyloxypropyltrimethoxysilane, methacryloxyoctyl-8-trimethoxysilane, γ-chloropropyltrimethoxysilane, γ-glycidoxypropyl-methoxysilane, hexamethyldisilazane, and the like.

[(c) Photopolymerization Initiator that Absorbs Activating Light Used in Irradiation in Shaping Step]

The photopolymerization initiator (c) has a function of generating a radical by means of activating light emitted from a light source mounted on a photofabrication apparatus, specifically, ultraviolet light or visible light, and causing the radical polymerization of the radically-polymerizable monomer (a). Accordingly, the photopolymerization initiator (c) needs, according to the type (wavelength) (Hereinafter, also referred to as "polymerization initiation wavelength") of the activating light used, to absorb the light and generate a radical.

An overly high content of the photopolymerization initiator (c) leads to the generation of burrs, etc. on the resultant three-dimensional manufactured product and degraded manufacturing accuracy. On the other hand, an overly low content of the photopolymerization initiator (c) render the manufacturing in the shaping step impossible. Therefore, the content of the photopolymerization initiator (c) needs to be 0.05 to 10.0 parts by mass relative to 100 parts by mass of the radically-polymerizable monomer (a). In order to more efficiently leave an effective amount of the photopolymerization initiator in the shaped product, the content of the polymerization initiator (c) is preferably 0.3 to 5.0 parts by mass, and more preferably 0.5 to 3.0 parts by mass, relative to 100 parts by mass of the radically-polymerizable monomer (a).

When the activating light used in the irradiation in the post-polymerization step has a wavelength different from that of the activating light used in the irradiation in the shaping step, the liquid photocurable resin composition preferably contains a photopolymerization initiator (c') that absorbs activating light used in the irradiation in the post-polymerization step, in addition to the photopolymerization initiator (c) that absorbs the activating light used in the irradiation in the shaping step. In this case, the content of the photopolymerization initiator (c') is preferably 0.05 to 5.0 parts by mass, more preferably 0.1 to 3.0 parts by mass, and still more preferably 0.3 to 1.0 parts by mass relative to 100 parts by mass of the radically-polymerizable monomer (a).

Any photopolymerization initiator that satisfies the requirements described above may be appropriately selected from known photopolymerization initiators and used. The photopolymerization initiator to be selected is not limited, and examples thereof include a self-cleaving photopolymerization initiator, a bimolecularly hydrogen-abstracting photopolymerization initiator, a photoacid generator, and combinations thereof. In addition, these photopolymerization initiators may be used in combination with a photosensitizing dye, an electron donating compound, or the like.

Examples of suitably usable self-cleaving photopolymerization initiators include: acylphosphine oxide compounds such as diphenyl(2,4,6-trimethylbenzoyl)-phosphine oxide and phenylbis(2,4,6-trimethylbenzoyl)-phosphine oxide; benzoketal compounds, benzyne compounds, α-aminoacetophenone compounds, α-hydroxyacetophenone compounds, titanocene compounds, acyloxime compounds; and the like. Examples of the photoacid generator include: iodonium salt compounds such as p-isopropylphenyl-p-methylphenyliodonium tetrakispentafluorophenylborate salt; sulfonium salt compounds such as dimethylphenacylsulfonium hexafluoroantimonate salt; halomethyl group-substituted triazine compounds such as 2,4,6-tris (trichloromethyl)-s-triazine; and the like. Examples of the photosensitizing dye include ketone compounds, coumarin dyes, cyanine dyes, merocyanine dyes, thiazine dyes, azine dyes, acridine dyes, xanthene dyes, squarylium dyes, pyrylium salt dyes, fused polycyclic aromatic compound (anthracene, perylene, etc.), thioxanthone compounds, and the like. Examples of the electron-donating compound include 4-dimethylaminobenzoic acid ester, 4-dimethylaminotoluene, p-dimethoxybenzene, 1,2,4-trimethoxybenzene, thiophene compounds, and the like.

In consideration of the fact that the wavelength of the activating light emitted from a light source mounted on a common photofabrication apparatus is 350 to 420 nm, and under the assumption that the shaping step is performed using a photofabrication apparatus having such a light source and the activating light having a wavelength of 450 to 490 nm is used for the irradiation in the post-polymerization step, phenylbis(2,4,6-trimethylbenzoyl)-phosphine oxide is preferably used as the photopolymerization initiator (c), and camphorquinone and an amine are preferably used as the photopolymerization initiator and (c').

[(d) Activating Light Absorbent that Absorbs Activating Light Used in Irradiation in Shaping Step]

In order to prevent excessive transmission of activating light emitted from a photofabrication apparatus and degradation of the manufacturing accuracy of the shaped product, the liquid photocurable resin composition needs to contain the activating light absorbent (d) that absorbs the activating light emitted from the photofabrication apparatus.

An overly high content of the activating light absorbent (d) leads to insignificant transmission of the activating light emitted from the light source of photofabrication apparatus through the liquid photocurable resin composition in the shaping step, and to the failure of the production of the three-dimensional manufactured product. On the other hand, an overly low content of the activating light absorbent (d) results in the degradation of the manufacturing accuracy of the resultant three-dimensional manufactured product. Therefore, the content of the activating light absorbent (d) needs to be 0.01 to 2.7 parts by mass relative to 100 parts by mass of the radically-polymerizable monomer (a). The content of the activating light absorbent (d) is preferably 0.04 to 3.0 parts by mass, more preferably 0.08 to 2.0 parts by mass, and still more preferably 0.25 to 1.0 parts by mass relative to 100 parts by mass of the radically-polymerizable monomer (a).

Since both the activating light absorbent (d) and the photopolymerization initiator (c) absorb the activating light emitted from the photofabrication apparatus, an increasing amount of the activating light absorbent (d) results in a decreasing amount of radicals generated from the photopolymerization initiator (c), and an increasing amount of the photopolymerization initiator (c) remaining in the shaped product immediately after the manufacturing. As described above, in the method for producing a three-dimensional manufactured product according to the present embodiment, radicals are generated from the remaining photopolymerization initiator (c) by the additional light irradiation after the photofabrication, and the radicals contribute to an increase in conversion during the additional heat treatment. Therefore, in the method for producing a three-dimensional manufactured product according to the present embodiment, the relationship between the amount of the photopolymerization initiator (c) and the amount of the activating light absorbent (d) is critically important in improving the mechanical strength of the final three-dimensional manufactured product.

As a result of intensive studies by the present inventors, the content of the activating light absorbent (d) is preferably 20 to 90% by mass, more preferably 30 to 80% by mass, and still more preferably 40 to 70% by mass relative to the content of the photopolymerization initiator (c), for leaving the photopolymerization initiator immediately after photofabrication in the shaping step and generating a sufficient amount of radicals upon the additional light irradiation in the post-polymerization step.

Any activating light absorbent (d) may be used without limitation as long as it absorbs activating light emitted from a light source mounted on a photofabrication apparatus, and examples thereof include: triazole compounds such as 2-(hydroxy-5-methylphenyl)-2H-benzotriazole and 2-(3-tert-butyl-2-hydroxy-5-methylphenyl)-5-chloro-2H-benzotriazole; benzophenone compounds such as 2,4-dihydroxybenzophenone and 2-hydroxy-4-methoxybenzophenone; and the like.

[(e) Polymerization Inhibitor]

The liquid photocurable resin composition needs to contain the polymerization inhibitor (e) in order to improve the storage stability of the liquid photocurable resin composition and prevent the radicals generated by the activating light from diffusing excessively in the shaping step and causing unnecessary portions to be cured.

An overly high content of the polymerization inhibitor (e) leads to insufficient curing of the liquid photocurable resin composition in the shaping step, resulting in poor manufacturing. On the other hand, an overly low amount of the polymerization inhibitor (e) results in impaired storage stability of the liquid photocurable resin composition and degraded manufacturing accuracy of the shaped product. Therefore, the content of the polymerization inhibitor (e) needs to be 0.01 to 5.0 parts by mass relative to 100 parts by mass of the radically-polymerizable monomer (a). The content of the polymerization inhibitor (e) is preferably 0.03 to 3.0 parts by mass, and more preferably 0.05 to 2.0 parts by mass, relative to 100 parts by mass of the radically-polymerizable monomer (a).

As described above, in the method for producing a three-dimensional manufactured product according to the present embodiment, the polymerization initiator (c) remaining in the shaped product generates radicals, leading to an increase in conversion in the post-polymerization step. Therefore, an overly large amount of the polymerization inhibitor (e) relative to the amount of the photopolymerization initiator (c) leads to the reaction of the radicals generated in the shaped product upon additional light irradiation with the polymerization inhibitor, and an insufficient increase in the conversion during the subsequent additional heating. In addition, an overly low amount of the polymerization inhibitor (e) relative to the amount of the photopolymerization initiator (c) results in an increase in the amount of the consumed photopolymerization initiator (c) in the shaping step, and hence the generation of an insufficient amount of radicals upon the additional light irradiation in the post-polymerization step, leading to an insufficient increase in the conversion. Therefore, the content of the polymerization inhibitor (e) is preferably 5 to 150 mass %, more preferably 8 to 120 mass %, and still more preferably 12 to 120 mass %, relative to the content of the photopolymerization initiator (c).

Any polymerization inhibitor (e) may be used without limitation as long as it reacts with a radical generated in the liquid photocurable resin composition to deactivate the radical, and examples thereof include di-tert-butyl-p-cresol, 4-methoxyphenol, and the like.

[Other Optional Components]

The liquid photocurable resin composition may contain other components such as a chain transfer agent, as needed. Examples of the chain transfer agent include α-methylstyrene dimers, and the like. The addition of the chain transfer agent tends to suppress the deformation due to polymerization shrinkage, and crack generation. On the other hand, an overly high content of the chain transfer agent may lead to a decrease in the rate of polymerization in the shaping step, and a failure to produce a shaped product by the irradiation with light from a photofabrication apparatus. Therefore, the content of the chain transfer agent is preferably 1.0 parts by mass or less, more preferably 0.5 parts by mass or less, and still more preferably 0.3 parts by mass or less relative to 100 parts by mass of the radically-polymerizable monomer (a).

<Requirement 2>

As described above, in the method for producing a three-dimensional manufactured product according to the present embodiment, it is important that the unreacted photopolymerization initiator (c) remains in the shaped product immediately after the shaping step, and that no photopolymerization initiator (c) remains in the three-dimensional manufactured product after the post-polymerization step.

Whether or not the photopolymerization initiator (c) remains can be determined by any method. For example, in the case where a photopolymerization initiator (c) exhibiting absorption in a visible light region such as phenylbis(2,4,6-trimethylbenzoyl)-phosphine oxide is used, it is observed that the phenylbis(2,4,6-trimethylbenzoyl)-phosphine oxide remaining in the shaped product immediately after the shaping step presents yellow coloration, and the yellow color fades out after the post-polymerization step. Alternatively, pulverizing a part of the resultant three-dimensional manufactured product, then subjecting it to the extraction with any suitable organic solvent, and analyzing the extraction liquid by a known analysis method (for example, high performance liquid chromatography, gas chromatography, or the like) also makes it possible to determine whether or not the photopolymerization initiator (c) remains.

The shaped product immediately after the shaping step is merely required to have a conversion sufficient to maintain the shape of the target three-dimensional manufactured product. For example, the shaped product has a conversion of preferably 55% or more, more preferably 60% or more, and still more preferably 65% or more. On the other hand, an overly high conversion in the shaped product may lead to degradation of the manufacturing accuracy of the resultant three-dimensional shaped product. Therefore, the shaped product has a conversion of preferably 95% or less, more preferably 90% or less, and still more preferably 85% or less.

<Requirement 3>

In the method for producing a three-dimensional manufactured product according to the present embodiment, the shaped product obtained in the shaping step is preferably washed with an organic solvent. The organic solvent is not limited, and examples thereof include: alcohol solvents such as ethanol, methanol, and isopropyl alcohol; ketone solvents such as acetone and methyl ethyl ketone; ether solvents such as diethyl ether, diisopropyl ether, and tetrahydrofuran; amide solvents such as N-methylpyrrolidone and dimethylacetamide; halogen-based solvents such as methylene chloride and chloroform; and the like. Among these, alcohol solvents are preferred from the viewpoint of high washing efficiency and low environmental load.

In the method for producing a three-dimensional manufactured product according to the present embodiment, the light irradiation and heating of the shaped product as the post-polymerization step is required.

The irradiation wavelength in the additional irradiation with light in the post-polymerization step is not limited as long as the photopolymerization initiator (c) remaining in the shaped product absorbs the light having the wavelength to generate a radical. The irradiation intensity in the additional light irradiation is preferably 5 mW/cm$^2$ or more, more preferably 10 mW/cm$^2$ or more, and still more preferably 30 mW/cm$^2$ or more, in order that the photopolymerization initiator (c) remaining in the shaped product generates a sufficient amount of radicals. On the other hand, an overly high irradiation intensity in the additional light irradiation leads to excessive heating of the shaped product, which causes cracks in the three-dimensional manufactured product. Therefore, the irradiation intensity is preferably 10,000 mW/cm$^2$ or less. The irradiation time of the additional light irradiation is not limited, and is preferably 1 minute or longer, more preferably 3 minutes or longer, and still more preferably 5 minutes or longer.

Heating of the shaped product simultaneously with the additional light irradiation in the post polymerization step is also preferred. The heating in this stage has an effect of accelerating decomposition of the photopolymerization initiator (c) remaining in the shaped product and thereby increasing the efficiency of the generation of the radicals. On the other hand, an overly high heating temperature in this stage may lead to rapid progress of the post-polymerization and crack generation in the three-dimensional manufactured product. Therefore, the lower limit of the heating temperature in the heating performed simultaneously with the light irradiation is preferably 37° C. or higher (especially 39° C. or higher), and the upper limit thereof is preferably 50° C. or lower (especially 45° C. or lower).

In the post-polymerization step, final curing by heating is necessary after the additional light irradiation of the shaped product. It is considered that in this heating, the conversion in the resultant three-dimensional manufactured product is increased by the reaction of the radicals generated during the additional light irradiation. Therefore, heating at higher temperature for a longer time period is preferred from the viewpoint of increasing the conversion more efficiently. On the other hand, an overly high heating temperature may lead to the generation of the cracks in the interior of the three-dimensional manufactured product due to polymerization shrinkage or deformation associated with a rapid increase in conversion. Further, heating for a long time period may be problematic in terms of a decrease in working efficiency. Therefore, the control of the heating temperature in the post-polymerization step is crucial for a three-dimensional manufactured product having no crack and high strength to be efficiently obtained.

The temperature is preferably controlled sequentially according to the following temperature conditions 1, 2, and 3, and the total heating time is preferably 5 minutes or longer, temperature condition 1:50° C. or higher and lower than 75° C. temperature condition 2:75° C. or higher and lower than 90° C. temperature condition 3:90° C. or higher and lower than 110° C.

The temperature condition 1 is preferably 55° C. or higher and lower than 70° C. The temperature condition 2 is preferably 75° C. or higher and lower than 85° C. The temperature condition 3 is preferably 90° C. or higher and lower than 100° C. The heating time under the temperature condition 1 is preferably 3 minutes to 120 minutes, and more preferably 5 minutes to 60 minutes. The heating time under the temperature condition 2 is preferably 3 minutes to 120 minutes, and more preferably 5 minutes to 60 minutes. The heating time under the temperature condition 3 is preferably 3 minutes to 120 minutes, and more preferably 5 minutes to 60 minutes.

Incidentally, when the total of the heating times under temperature conditions 1 and 2 is 10 minutes or longer, a selection not to perform the temperature condition 3 may be acceptable, and when the heating time under the temperature condition 1 is 15 minutes or longer, a selection not to perform the temperature conditions 2 and 3 may be acceptable.

In the method for producing a three-dimensional manufactured product according to the present embodiment, the mechanical strength of the resultant three-dimensional manufactured product is improved by subjecting the shaped product to the additional light irradiation and the additional heating to increase the conversion in the three-dimensional manufactured product. Therefore, a high conversion in the three-dimensional manufactured product is preferred. The conversion in the three-dimensional manufactured product generation, and the use of the three-dimensional manufactured product as a crown restoration material is particularly preferred.

EXAMPLES

Hereinafter, the present invention will be described more specifically by way of examples, but the present invention is not limited to these examples.

Compounds used in Examples and Comparative Examples and abbreviations thereof are shown below.
(a) Photopolymerizable Monomer
 D-2.6E: bisphenol A ethylene glycol (EO) adduct dimethacrylate (number of EO added: average 2.6)
 UDMA: urethane dimethacrylate
 3G: triethylene glycol dimethacrylate
(b) Inorganic Filler
 F-1: γ-methacryloyloxypropyltrimethoxysilane surface treated product of spherical silica-zirconia particles (average particle diameter: 0.5 μm)
 F-2: γ-methacryloyloxypropyltrimethoxysilane surface treated product of spherical silica-zirconia particles (average particle diameter: 0.08 μm)
(c) Photopolymerization Initiator
 BAPO: Bisacylphosphine oxide
(d) Activating Light Absorbent
 SS3:2-(3-tert-butyl-2-hydroxy-5-methylphenyl)-5-chloro-2H-benzotriazole
(e) Polymerization Inhibitor
 BHT: Dibutylhydroxytoluene
 HOME: Hydroquinone methyl ether

Example 1

To 100 parts by mass of the polymerizable monomers (mixing mass ratio:D-2.6E/UDMA/3G=30/50/20), the components shown in Table 1 were added in the amounts shown in Table 1, and the mixture was stirred under red light until uniform, followed by defoaming to prepare a liquid photocurable resin composition.

TABLE 1

| Component | (a) | | | (b) | | (c) | (d) | (e) | |
|---|---|---|---|---|---|---|---|---|---|
| Substance | D-2.6E | UDMA | 3G | F-1 | F-2 | BAPO | SS3 | HQME | BHT |
| Parts by mass | 30 | 50 | 20 | 105 | 45 | 1.4 | 0.7 | 0.1 | 0.1 |
| Mass ratio relative to (c) (%) * | | — | | | — | | 50.0 | 14.3 | |

* {parts by mass of (d)/parts by mass of (c)} × 100 (%) or {parts by mass of (e)/parts by mass of (c)} × 100 (%)

is, for example, preferably 80% or more, more preferably 85% or more, and still more preferably 88% or more.

<Method for Producing Dental Restoration>

The resultant three-dimensional manufactured product is characterized by having a high conversion and being substantially crack free in the interior and on the surface thereof, and has high mechanical strength. Therefore, the resultant three-dimensional manufactured product can be used for various applications, and is also suitable for use in a dental restoration material. Exemplary dental restoration materials in which the resultant three-dimensional manufactured product may be suitably used include denture materials, crown restoration materials, and the like. A smaller size of the three-dimensional manufactured product is more advantageous from the viewpoint of the suppression of the crack Subsequently, a shaped product having a predetermined shape (made of a cured product of the liquid photocurable resin composition) was obtained by a 3D printer (from DWS: DW029D) using the resultant liquid photocurable resin composition, and after washing, the shaped product was subjected to post-polymerization under the post-polymerization step conditions shown in Table 2, to produce a bending test specimen (a rectangular cured product having a size of 2.05 mm×2.05 mm×25.05 mm) and a test specimen for conversion determination and crack evaluation (a discoidal cured product having a diameter of 15 mm and a thickness of 1.0 mm).

The test specimens obtained thus were subjected to bending strength measurement, conversion determination, and crack evaluation as described below. The evaluation results are shown in Table 3.

(1) Bending Strength Measurement

The cured product prepared as the bending test specimen was formed into a prism of 2 mm×2 mm×25 mm using a waterproof abrasive paper 800 grit, and the sample piece was mounted on a tester (Autograph AG5000D, from Shimadzu Corporation), and the three-point bending fracture strength thereof was measured at a support span of 20 mm and a crosshead speed of 1 mm/min.

(2) Conversion Determination

A near infrared spectrum was measured on the cured product prepared as the test specimen for conversion determination and crack evaluation in a transmission mood as described below, to calculate the conversion in the cured product.

Near-infrared spectroscopy (NIR measurement) was performed on each of the paste before polymerization (BP) and the final manufactured product (MP), and the peak areas of the absorption peak of =C–H appearing at a wavenumber of around 6165 cm$^{-1}$ assigned to the double bond in the resultant measurement chart, S(HSP2) BP and S(HSP2) MP, were determined. Additionally, the peak areas of the absorption peak appearing at a wavenumber of around 4920 cm$^{-1}$ assigned to —NH— in the urethane bond present in the polymerizable monomer, S(NH) BP and S(NH) MP, were determined. Then, the conversion R (%) was calculated according to the following equations:

$$R\,(\%) = 100 - 100 \times \{S(HSP2/NH)MP\}/\{S(HSP2/NH)BP\}$$

$$S(HSP2/NH)BP = \{S(HSP2)BP\}/\{S(NH)BP\}$$

$$S(HSP2/NH)MP = \{S(HSP2)MP\}/\{S(NH)MP\}$$

The NIR measurement was performed using Spectrum One from Perkin Elmer as a measuring instrument under the conditions of a number of scans of 4 and a resolution of 4 cm$^{-1}$.

In addition, the conversion in the shaped product immediately after the photofabrication was also determined similarly to the test specimen for conversion determination and crack evaluation.

(3) Crack Evaluation

The cured product prepared as the test specimen for conversion determination and crack evaluation was observed under a microscope to evaluate the presence or absence of a crack on the surface of the cured product. Further, the same cured product was polished by 100 to 500 μm in the depth direction, and the polished surface was observed under a microscope every 100 μm to evaluate the presence or absence of a crack in the interior of the cured product. The evaluation criteria for the crack evaluation are as follows.

—Evaluation Criteria—

A: no crack being found on the surface and in the interior of the cured product.

B: crack(s) being found only on the surface of cured product.

C: cracks being found on the surface and in the interior of the cured product.

Examples 2 to 11 and Comparative Examples 1 to 2

Test specimens were prepared and evaluated in the same manner as in Example 1 except that the conditions in the post-polymerization step were changed to those shown in Table 2. The results are shown in Table 3.

TABLE 2

| | | | Conditions for post-polymerization step | | | |
| | | | | Heating after light irradiation | | |
| No. | | Light irradiation | Temperature condition 1 | Temperature condition 2 | Temperature condition 3 |
| --- | --- | --- | --- | --- | --- |
| Examples | 1 | LED light source (Maximum wavelength: 400-408 nm, 465-475 nm) Irradiation intensity: 90 mW/cm² Heating: 40° C. 10 min | 60° C. 5 min | 80° C. 5 min | 90° C. 5 min |
| | 2 | LED light source (Maximum wavelength: 400-408 nm, 465-475 nm) Irradiation intensity: 90 mW/cm² Heating: 40° C. 10 min | 60° C. 10 min | 80° C. 5 min | Not applied |
| | 3 | LED light source (Maximum wavelength: 400-408 nm, 465-475 nm) Irradiation intensity: 90 mW/cm² Heating: 40° C. 10 min | 60° C. 5 min | 80° C. 10 min | Not applied |
| | 4 | LED light source (Maximum wavelength: 400-408 nm, 465-475 nm) Irradiation intensity: 90 mW/cm² Heating: 40° C. 10 min | 60° C. 15 min | Not applied | Not applied |
| | 5 | LED light source (Maximum wavelength: 400-408 nm, 465-475 nm) Irradiation intensity: 90 mW/cm² Heating: 25° C. 10 min | 60° C. 5 min | 80° C. 5 min | 90° C. 5 min |
| | 6 | LED light source (Maximum wavelength: 400-408 nm, 465-475 nm) Irradiation intensity: 90 mW/cm² Heating: 25° C. 10 min | 60° C. 10 min | 80° C. 5 min | Not applied |
| | 7 | LED light source (Maximum wavelength: 400-408 nm, 465-475 nm) Irradiation intensity: 90 mW/cm² Heating: 25° C. 10 min | 60° C. 5 min | 80° C. 10 min | Not applied |

TABLE 2-continued

| | | Conditions for post-polymerization step | | |
| | | | Heating after light irradiation | | |
| No. | Light irradiation | Temperature condition 1 | Temperature condition 2 | Temperature condition 3 |
|---|---|---|---|---|
| | 8 LED light source (Maximum wavelength: 400-408 nm, 465-475 nm) Irradiation intensity: 90 mW/cm$^2$ Heating: 25° C. 10 min | 60° C. 15 min | Not applied | Not applied |
| | 9 LED light source (Maximum wavelength: 400-408 nm, 465-475 nm) Irradiation intensity: 90 mW/cm$^2$ Heating: 25° C. 10 min | 60° C. 1 min | 80° C. 5 min | 90° C. 5 min |
| | 10 LED light source (Maximum wavelength: 400-408 nm, 465-475 nm) Irradiation intensity: 90 mW/cm$^2$ Heating: 25° C. 10 min | Not applied | Not applied | 90° C. 15 min |
| | 11 LED light source (Maximum wavelength: 400-408 nm, 465-475 nm) Irradiation intensity: 90 mW/cm$^2$ Heating: 25° C. 10 min | Not applied | 80° C. 15 min | Not applied |
| Comparative Examples | 1 Not applied | 60° C. 10 min | 80° C. 5 min | Not applied |
| | 2 LED light source (Maximum wavelength: 400-408 nm, 465-475 nm) Irradiation intensity: 90 mW/cm$^2$ Heating: 25° C. 10 min | Not applied | Not applied | Not applied |

TABLE 3

| No. | | Bending strength (Mpa) [standard deviation] | Conversion (%) Immediately after photofabrication | Conversion (%) Final manufactured product | Crack evaluation |
|---|---|---|---|---|---|
| Examples | 1 | 190 [8] | 75 | 94 | A |
| | 2 | 193 [9] | 75 | 93 | A |
| | 3 | 197 [4] | 75 | 95 | A |
| | 4 | 193 [5] | 75 | 92 | A |
| | 5 | 182 [6] | 75 | 89 | A |
| | 6 | 186 [5] | 75 | 91 | A |
| | 7 | 188 [6] | 75 | 93 | A |
| | 8 | 190 [10] | 75 | 93 | A |
| | 9 | 161 [15] | 75 | 89 | A |
| | 10 | 150 [28] | 75 | 86 | A |
| | 11 | 142 [20] | 75 | 84 | B |
| Comparative Examples | 1 | 110 [18] | 75 | 79 | C |
| | 2 | 120 [19] | 75 | 79 | A |

As shown in Table 3, in Examples 1 to 11, in which the light irradiation and the subsequent heat treatment were performed in the post-polymerization step, the conversions in the shaped product and in the three-dimensional manufactured product were high, the mechanical strength was excellent, and no crack was found in the interior of the three-dimensional manufactured product.

On the other hand, in Comparative Example 1, in which only the heat treatment was performed in the post-polymerization step, and Comparative Example 2, in which only the light irradiation was performed in the post-polymerization step, the conversion in the three-dimensional manufactured product was lower than in Examples 1 to 11, and the mechanical strength was inferior. Furthermore, in Comparative Example 1, cracks were found in the interior and on the surface of the three-dimensional manufactured product.

Examples 12 to 22 and Comparative Examples 3 to 6

Liquid photocurable resin compositions were prepared in the same manner as in Example 1 except that the composition was changed as shown in Table 4. Then, the resultant liquid photocurable resin compositions were used to prepare and evaluate test specimens in the same manner as in Example 1. The results are shown in Table 5.

TABLE 4

| No. | | (a) D-2.6E (parts by mass) | (a) UDMA (parts by mass) | (a) 3G (parts by mass) | (b) F-1 (parts by mass) | (b) F-2 (parts by mass) | (c) BAPO (parts by mass) | (d) SS3 (parts by mass) | (d) Mass ratio relative to (c) (%) | (e) HQME (parts by mass) | (e) BHT (parts by mass) | (e) Mass ratio relative to (c) (%) |
|---|---|---|---|---|---|---|---|---|---|---|---|---|
| Examples | 12 | 30 | 50 | 20 | 105 | 43 | 0.7 | 0.5 | 71.4 | 0.1 | 0.1 | 28.6 |
| | 13 | 30 | 50 | 20 | 105 | 45 | 1.4 | 0.7 | 50.0 | 1.0 | 1.0 | 142.9 |
| | 14 | 30 | 50 | 20 | 105 | 45 | 1.4 | 1.2 | 85.7 | 0.1 | 0.1 | 14.3 |
| | 15 | 30 | 50 | 30 | 105 | 45 | 1.4 | 0.3 | 21.4 | 0.1 | 0.1 | 14.3 |
| | 16 | 30 | 50 | 20 | 105 | 45 | 1,4 | 0.7 | 50.0 | 0.1 | 0.1 | 14.3 |
| | 17 | 30 | 50 | 20 | 185 | 45 | 1.4 | 0.1 | 7.1 | 0.1 | 0.1 | 14.3 |
| | 18 | 30 | 50 | 20 | 105 | 45 | 1.4 | 0.7 | 50.0 | 0.04 | 0.04 | 5.7 |
| | 19 | 30 | 50 | 20 | 105 | 45 | 0.6 | 1.2 | 200.0 | 0.1 | 0.1 | 33.3 |
| | 20 | 30 | 50 | 20 | 70 | 30 | 1.4 | 0.7 | 50.0 | 0.1 | 0.1 | 14.3 |
| | 21 | 30 | 50 | 20 | 47 | 20 | 1.4 | 0.7 | 50.0 | 0.1 | 0.1 | 14.3 |
| | 22 | 30 | 50 | 20 | 28 | 12 | 1.4 | 0.7 | 200.0 | 0.1 | 0.1 | 33.3 |

TABLE 4-continued

| No. | | (a) D-2.6E (parts by mass) | UDMA (parts by mass) | 3G (parts by mass) | (b) F-1 (parts by mass) | F-2 (parts by mass) | (c) BAPO (parts by mass) | (d) SS3 (parts by mass) | Mass ratio relative to (c) (%) | (e) HQME (parts by mass) | BHT (parts by mass) | Mass ratio relative to (c) (%) |
|---|---|---|---|---|---|---|---|---|---|---|---|---|
| Comparative | 3 | 30 | 50 | 20 | 105 | 45 | 1.4 | 2.8 | 300.0 | 0.1 | 0.1 | 14.3 |
| Examples | 4 | 30 | 50 | 20 | 105 | 45 | 1.4 | 0.005 | 0.4 | 0.1 | 0.1 | 14.3 |
| | 5 | 30 | 50 | 28 | 105 | 45 | 1.4 | 0.7 | 50.0 | 3.0 | 3.0 | 428.6 |
| | 6 | 30 | 50 | 20 | 205 | 45 | 1.4 | 0.7 | 50.0 | 0.004 | 0.004 | 0.6 |

TABLE 5

| No. | | Bending strength (Mpa) [standard deviation] | Conversion (%) Immediately after photofabrication | Final manufactured product | Crack evaluation |
|---|---|---|---|---|---|
| Examples | 12 | 188 [12] | 73 | 89 | A |
| | 13 | 192 [4] | 71 | 92 | A |
| | 14 | 190 [5] | 73 | 92 | A |
| | 15 | 182 [6] | 75 | 89 | A |
| | 16 | 195 [3] | 70 | 91 | A |
| | 17 | 153 [6] | 76 | 86 | A |
| | 18 | 150 [12] | 77 | 85 | A |
| | 19 | 147 [6] | 75 | 85 | A |
| | 20 | 185 [4] | 75 | 95 | A |
| | 21 | 160 [8] | 77 | 95 | A |
| | 22 | 147 [6] | 78 | 96 | A |
| Comparative | 3 | 116 [15] | 64 | 84 | B |
| Examples | 4 | 117 [21] | 72 | 80 | B |
| | 5 | 112 [20] | 65 | 78 | B |
| | 6 | 121 [12] | 77 | 84 | C |

As shown in Table 5, in Examples 12 to 22, in which the amounts of the added activating light absorbent (SS3) and the added polymerization inhibitor (HOME, BHT) were appropriately adjusted, the conversions in the shaped product and the three-dimensional manufactured product were high, the mechanical strength was excellent, and no crack was found in the interior and on the surface of the three-dimensional shaped manufactured product.

On the other hand, in Comparative Example 3, in which the amount of the added activating light absorbent (SS3) was large, and Comparative Example 5, in which the amount of the added polymerization inhibitor (HOME, BHT) was large, the conversions in the shaped product and in the three-dimensional manufactured product were lower in than in Examples 12 to 22, and the mechanical strength was inferior. In Comparative Example 4, in which the amount of the added active light absorbent (SS3) was small, and Comparative Example 6, in which the amount of the added polymerization inhibitor (HOME, BHT) was small, although the conversion in the shaped product was high, the conversion in the three-dimensional shaped manufactured product was lower than in Examples 12 to 22, and the mechanical strength was inferior. Furthermore, in Comparative Example 6, cracks were found in the interior and on the surface of the three-dimensional manufactured product.

The invention claimed is:

1. A method for producing a three-dimensional manufactured product, the method comprising:

a shaping step of digitizing and ordinating a height direction of a three-dimensional object and generating two-dimensional shape data indicating a cross-sectional shape of the three-dimensional object at each ordinated height, based on three-dimensional shape data indicating a shape of the three-dimensional object, and sequentially forming and stacking manufactured layers each having a shape corresponding to the two-dimensional shape at each height based on the two-dimensional shape data, according to the order of the ordinating, using a vat photopolymerization process wherein a predetermined position of a liquid photocurable resin composition held in a vat is irradiated with activating light being ultraviolet light or visible light to selectively cure the liquid photocurable resin composition present in the position, to obtain a shaped product comprising a cured product of the liquid photocurable resin composition having a shape corresponding to the shape of the three-dimensional object; and a post-polymerization step of polymerizing an unpolymerized component comprised in the shaped product, wherein the liquid photocurable resin composition comprises:

100 parts by mass of a radically-polymerizable monomer (a);

100 to 200 parts by mass of an inorganic filler (b);

0.05 to 10.0 parts by mass of a photopolymerization initiator (c) that absorbs the activating light to generate a radical;

0.01 to 2.7 parts by mass of an activating light absorbent (d) that absorbs the activating light; and 0.01 to 5.0 parts by mass of a polymerization inhibitor (e), and wherein in the shaping step, the activating light absorbent (d) in an amount of 20 to 90% by mass relative to the amount of the photopolymerization initiator (c), and the polymerization inhibitor (e) in an amount of 8 to 150% by mass relative to the amount of the photopolymerization initiator (c) is used to obtain the shaped product comprising an effective amount of the photopolymerization initiator (c), and the post-polymerization step comprises irradiating the shaped product with the activating light at an irradiation intensity of 10 to 10,000 mW/cm$^2$ and then heating the shaped product irradiated with the activating light at a temperature of 50° C. or higher and lower than 110° C.

2. The method for producing a three-dimensional manufactured product according to claim 1, wherein the vat photopolymerization process comprises:

a first step of irradiating a predetermined position of the liquid photocurable resin composition held in the vat with the activating light and curing the liquid photocurable resin composition, based on the two-dimensional shape data at a first ordinate height in an ordinating order, to form a manufactured layer having a shape corresponding to the two-dimensional shape data, wherein the manufactured layer is a prebonding layer;

a second step of moving the prebonding layer upward or downward to supply the liquid photocurable resin composition directly above or below the prebonding layer in the vat;

a third step of irradiating a predetermined position of the liquid photocurable resin composition supplied directly above or below the prebonding layer with the activating light and curing the liquid photocurable resin composition, based on two-dimensional shape data at a height of the next ordinate in the ordinating order following the immediately preceding step, and thereby forming a new manufactured layer having a shape corresponding to the two-dimensional shape data, and concurrently bonding the new manufactured layer to the prebonding layer, to obtain a stack having the new manufactured layer as a new prebonding layer; and a fourth step of moving the stack upward or downward to supply the liquid photocurable resin composition directly above or below the new prebonding layer in the vat, and a cycle consisting of the third step and the fourth step is repeated using the new prebonding layer as the prebonding layer in the third step, and in a last third step, a new manufactured layer is formed based on two-dimensional shape data at a height of the last ordinate in the ordinating order, to obtain a stack.

3. The method for producing a three-dimensional manufactured product according to claim 1, further comprising a washing step of washing the shaped product after the shaping step and before the post-polymerization step.

4. A method for producing a dental restoration, comprising producing the dental restoration according to the method for producing a three-dimensional manufactured product according to claim 1.

* * * * *